United States Patent [19]
Weigel

[11] Patent Number: 5,844,119
[45] Date of Patent: *Dec. 1, 1998

[54] GENETICALLY MODIFIED PLANTS HAVING MODULATED FLOWER DEVELOPMENT

[75] Inventor: Detlef Weigel, Del Mar, Calif.

[73] Assignee: The Salk Institute for Biological Studies, San Diego, Calif.

[*] Notice: The term of this patent shall not extend beyond the expiration date of Pat. No. 5,637,785.

[21] Appl. No.: 576,156

[22] Filed: Dec. 21, 1995

Related U.S. Application Data

[63] Continuation-in-part of Ser. No. 360,336, Dec. 21, 1994, Pat. No. 5,637,785.

[51] Int. Cl.$^6$ .............................. A01H 5/00; C12N 5/04; C12N 15/29; C12N 15/82
[52] U.S. Cl. ................... 800/205; 800/250; 435/69.1; 435/172.3; 435/320.1; 435/419; 536/23.6; 536/24.1
[58] Field of Search .................................. 800/205, 250; 435/69.1, 70.1, 172.3, 240.4, 320.1, 419; 536/23.6, 24.1

[56] References Cited

U.S. PATENT DOCUMENTS 4,513,532  4/1985  Muirhead, Jr. et al. .................... 47/58

OTHER PUBLICATIONS

Weigel et al. 1995. Nature 377:495–500.
Mandel et al. 1995. Nature 377:522–524.
Weigel et al. 1993. pp. 93–107 In: Molec. Basis Morphogenesis, Wiley–Liss, Inc.
Smith, et al., Nature, 334:724, 1988.
Napoli, et al., Plant Cell, 2:279, 1990.
Angenent, et al., Plant Journal, 4(1):101, 1993.
Weigel, et al., *LEAFY Controls Floral Meristem Identity in Arabidopsis*, Cell, 69:843, 1992.
Mandel, et al., *Molecular characterization of the Arabidopsis floral hemeotic gene APETALA1*, Nature, 360:273, 1992.
Coen, et al., *Floricaula: A Homeotic Gene Required for Flower Development in Antirrhinum majus*, Cell, 63:1311, 1990.
Bowman, et al., *Control of flower development in Arabidopsis thaliana by APETALA1 and interacting genes*, Development, 119:721, 1993.
Bechtold, et al., *In Plants Agrobacterium mediated gene transfer by infiltration of adult Arabidopsis thaliana plants*, C.R. Acad. Sci. Paris, Sciences de la vie/Life Sciences, 316:1194, 1993.
Weigel and Meyerowitz, *Genetic Hierarchy Controlling Flower Development, Molecular Basis of Morphogenesis*, Wiley–Liss, Inc., pp. 93–107, 1993.

*Primary Examiner*—David T. Fox
*Attorney, Agent, or Firm*—Fish & Richardson, P.C.

[57] ABSTRACT

The present invention provides a genetically modified plant and a method for producing such a plant characterized as having modulated flower meristem development. As an illustrative example, the invention provides genetically modified tobacco and aspen plants characterized as having early floral meristem development and comprising a structural gene encoding the LEAFY protein in its genome.

28 Claims, 6 Drawing Sheets

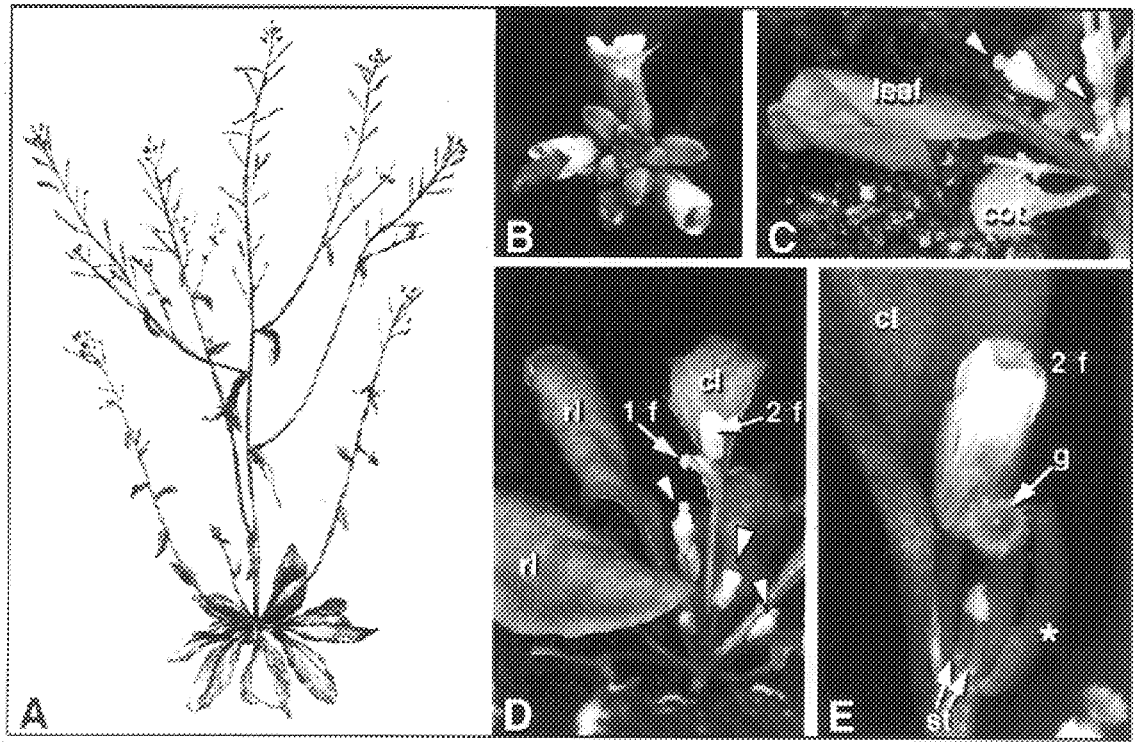

FIG. 7A
FIG. 7B
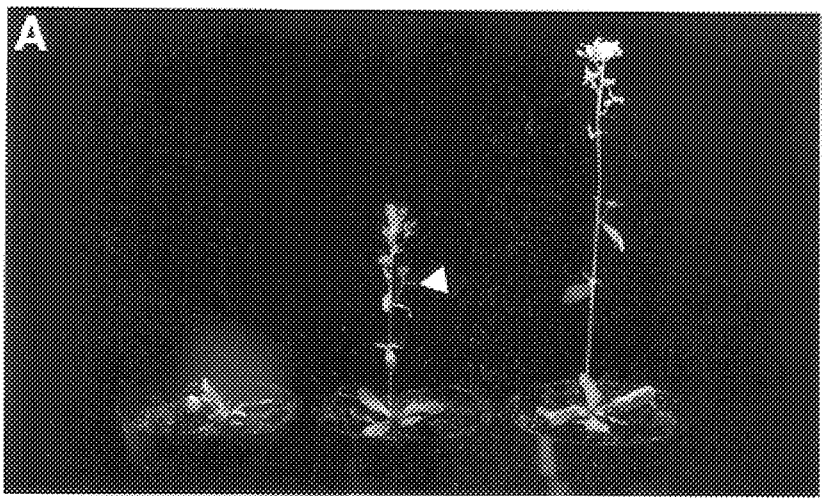
FIG. 7C
FIG. 7D

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1054
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
ctttccaatt ggttcatacc aaagtctgag ctcttcttta tatctctctt gtagtttct      60
attgggggtc tttgttttgt ttggttcttt tagagtaaga agtttcttaa aaaaggata     120
aaaatgggaa ggggtagggt tcaattgaag aggatagaga acaagatcaa tagacaagg     180
acattctcga aaagaagagc tggtcttttg aagaaagctc atgagatctc tgttctctt     240
gatgctgaag ttgctcttgt tgtcttctcc cataagggga aactcttcga atactccat     300
gattcttgta tggagaagat acttgaacgc tatgagaggt actcttacgc cgaaagacg     360
cttattgcac ctgagtccga cgtcaataca aactggtcga tggagtataa caggcttag     420
gctaagattg agcttttgga gagaaaccag aggcattatc ttggggaaga cttgcaaga     480
atgagcccta aagagcttca gaatctggag cagcagcttg acactgctct taagcacac     540
cgcactagaa aaaccaact tatgtacgag tccatcaatg agctccaaaa aaaggagag     600
gccatacagg agcaaaacag catgctttct aaacagatca aggagaggga aaaaattct     660
agggctcaac aggagcagtg ggatcagcag aaccaaggcc acaatatgcc tccccctcg     720
ccaccgcagc agcaccaaat ccagcatcct tacatgctct ctcatcagcc atctccttt     780
ctcaacatgg gtggtctgta tcaagaagat gatccaatgg caatgaggaa tgatctcga     840
ctgactcttg aacccgttta caactgcaac cttggctgct tcgccgcatg aagcatttc     900
atatatatat ttgtaatcgt caacaataaa aacagtttgc cacatacata taaatagtg     960
ctaggctctt ttcatccaat taatatattt tggcaaatgt tcgatgttct tatatcaca    1020
tatataaatt agcaggctcc tttcttttt tgta                                1054
```

( 2 ) INFORMATION FOR SEQ ID NO:2:

( i ) SEQUENCE CHARACTERISTICS:
        ( A ) LENGTH: 255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Arg Gly Arg Val Gln Leu Lys Arg Ile Glu Asn Lys Ile Asn
 1               5                  10                  15
Arg Gln Val Thr Phe Ser Lys Arg Arg Ala Gly Leu Leu Lys Lys Ala
            20                  25                  30
His Glu Ile Ser Val Leu Cys Asp Ala Glu Val Ala Leu Val Val Phe
        35                  40                  45
Ser His Lys Gly Lys Leu Phe Glu Tyr Ser Thr Asp Ser Cys Met Glu
    50                  55                  60
Lys Ile Leu Glu Arg Tyr Glu Arg Tyr Ser Tyr Ala Glu Arg Gln Leu
65                  70                  75                  80
```

-continued

| | | | | | | | | | | | | | | |
|---|---|---|---|---|---|---|---|---|---|---|---|---|---|---|
| Ile | Ala | Pro | Glu | Ser 85 | Asp | Val | Asn | Thr | Asn 90 | Trp | Ser | Met | Glu | Tyr 95 | Asn |
| Arg | Leu | Lys | Ala 100 | Lys | Ile | Glu | Leu | Leu 105 | Glu | Arg | Asn | Gln | Arg 110 | His | Tyr |
| Leu | Gly | Glu 115 | Asp | Leu | Gln | Ala | Met 120 | Ser | Pro | Lys | Glu | Leu 125 | Gln | Asn | Leu |
| Glu | Gln 130 | Gln | Leu | Asp | Thr | Ala 135 | Leu | Lys | His | Ile | Arg 140 | Thr | Arg | Lys | Asn |
| Gln 145 | Leu | Met | Tyr | Glu | Ser 150 | Ile | Asn | Glu | Leu | Gln 155 | Lys | Lys | Glu | Lys | Ala 160 |
| Ile | Gln | Glu | Gln | Asn 165 | Ser | Met | Leu | Ser | Lys 170 | Gln | Ile | Lys | Glu | Arg 175 | Glu |
| Lys | Ile | Leu | Arg 180 | Ala | Gln | Gln | Glu | Gln 185 | Trp | Asp | Gln | Gln | Asn 190 | Gln | Gly |
| His | Asn | Met 195 | Pro | Pro | Pro | Leu | Pro 200 | Pro | Gln | Gln | His | Gln 205 | Ile | Gln | His |
| Pro | Tyr 210 | Met | Leu | Ser | His | Gln 215 | Pro | Ser | Pro | Phe | Leu 220 | Asn | Met | Gly | Gly |
| Leu 225 | Tyr | Gln | Glu | Asp | Asp 230 | Pro | Met | Ala | Met | Arg 235 | Asn | Asp | Leu | Glu | Leu 240 |
| Thr | Leu | Glu | Pro | Val 245 | Tyr | Asn | Cys | Asn | Leu 250 | Gly | Cys | Phe | Ala | Ala 255 | |

GENETICALLY MODIFIED PLANTS HAVING MODULATED FLOWER DEVELOPMENT

This application is a continuation-in-part of U.S. patent application Ser. No. 08/360,336 filed on Dec. 21, 1994., now U.S. Pat. No. 5,637,785.

BACKGROUND OF THE INVENTION

1. Field of the Invention

The invention relates generally to plant genetic engineering, and specifically to novel genetically engineered plants characterized as having a phenotype of early flower meristem development, and methods for producing such plants.

2. Description of Related Art

Most angiosperm species are induced to flower in response to environmental stimuli such as day length and temperature, and internal cues, such as age. Adult organs of flowering plants develop from groups of stem cells called meristems. The identity of a meristem is inferred from structures it produces: vegetative meristems give rise to roots and leaves, inflorescence meristems give rise to flower meristems, and flower meristems give rise to floral organs such as sepals and petals. Not only are meristems capable of generating new meristems of different identity, but their own identity can change during development. For example, a vegetative shoot meristem can be transformed into an inflorescence meristem upon floral induction, and in some species, the inflorescence meristem itself will eventually become a flower meristem. Despite the importance of meristem transitions in plant development, little is known about the underlying mechanisms.

Following germination, the shoot meristem produces a series of leaf meristems on its flanks. However, once floral induction has occurred, the shoot meristem switches to the production of flower meristems. Flower meristems produce floral organ primordia, which develop individually into sepals, petals, stamens or carpels. Thus, flower formation can be thought of as a series of distinct developmental steps, i.e. floral induction, the formation of flower primordia and the production of flower organs. Mutations disrupting each of the steps have been isolated in a variety of species, suggesting that a genetic hierarchy directs the flowering process (see for review, Weigel and Meyerowitz, In *Molecular Basis of Morphogenesis* (ed. M. Bemfield). 51st Annual Symposium of the Society for Developmental Biology, pp. 93–107, New York, 1993).

Recently, studies of two distantly related dicotyledons, *Arabidopsis thaliana* and *Antirrhinum majus,* led to the identification of three classes of homeotic genes, acting alone or in combination to determine floral organ identity (Bowman, et al., *Development,* 112: 1, 1991; Carpenter and Coen, *Genes Devl.,* 4:1483, 1990; Schwarz-Sommer, et al., *Science,* 250:931, 1990). Several of these genes are transcription factors whose conserved DNA-binding domain has been designated the MADS box (Schwarz-Sommer, et al., supra).

Earlier acting genes that control the identity of flower meristems have also been characterized. Flower meristems are derived from inflorescence meristems in both Arabidopsis and Antirrhinum. Two factors that control the development of meristematic cells into flowers are known. In Arabidopsis, the factors are the products of the LEAFY gene (Weigel, et al., *Cell* 69:843, 1992) and the APETALA1 gene (Mandel, et al., *Nature* 360:273, 1992, herein incorporated by reference in its entirety and SEQ ID NO:1 and 2). When either of these genes is inactivated by mutation, structures combining the properties of flowers and inflorescence develop (Weigel, et al., supra; Irish and Sussex, *Plant Cell,* 2:741, 1990). In Antirrhinum, the homologue of the Arabidopsis LEAFY gene is FLORICA ULA (Coen, et al., *Cell,* 63:1311, 1990) and that of the APETALA1 gene is SQUAMOSA (Huijser, et al., *EMBO J,* 11: 1239, 1992). The latter pair contains MADS box domains.

LEAFY is expressed very early in floral anlagen and floral primordia, consistent with it having a direct role in establishing floral meristem identity. In the developing floral primordium, LEAFY expression is detected much earlier than expression of the homeotic genes AG and AP3, suggesting that LEAFY plays a role in controlling the expression of floral homeotic genes.

There is increasing incentive by those working in the field of plant biotechnology to successfully genetically engineer plants, including the major crop varieties. One genetic modification that would be economically desirable would be to accelerate the flowering time of a plant. Induction of flowering is often the limiting factor for growing crop plants. One of the most important factors controlling induction of flowering is day length, which varies seasonally as well as geographically. There is a need to develop a method for controlling and inducing flowering in plants, regardless of the locale or the environmental conditions, thereby allowing production of crops, at any given time. Since most crop products (e.g., seeds, grains, fruits), are derived from flowers, such a method for controlling flowering would be economically invaluable.

SUMMARY OF THE INVENTION

The present invention arose out of the discovery that a genetically modified plant cell could be produced, from which a whole plant can be regenerated which stably incorporates a flower development genetic trait introduced into the plant cell. Specifically, the trait of early flowering can be imparted on a plant by genetic modification according to the method of the invention.

In a first embodiment, the present invention provides a genetically modified plant comprising at least one heterologous nucleic acid sequence in its genome and characterized as having modulated floral meristem development. Preferably, the plant is genetically modified by introduction of a nucleic acid sequence encoding the LEAFY protein. Alternatively, the plant is genetically modified by transformation with a nucleic acid sequence encoding the LEAFY protein or a nucleic acid sequence encoding the APETALA1 protein, or both. The invention also provides plant cells, plant tissue and seeds derived from the genetically modified plant.

In a second embodiment, the invention provides a vector (s) for transformation of a plant cell to modulate flower meristem development, wherein said vector(s) comprises a nucleic acid sequence comprising at least one structural gene encoding a protein that modulates flower meristem development, operably associated with a promoter. Preferably, the vector comprises a nucleic acid sequence encoding the LEAFY protein.

Also provided is a method of producing a genetically modified plant characterized as having modulated flower meristem development. The method comprises contacting a plant cell with a vector(s), comprising a nucleic acid sequence comprising at least one structural gene encoding a protein for modulating flower meristem development, operably associated with a promoter to obtain a transformed plant cell; producing plants from said transformed plant cell; and selecting a plant exhibiting modulated flower meristem development.

BRIEF DESCRIPTION OF THE DRAWINGS

FIGS. 5A–5E show the conversion of all shoots into flowers in 35S::LFY Arabidopsis plants. Panel (A), For comparison, a drawing of a mature Arabidopsis plant (Nossen ecotype) of about six weeks of age is shown. Panel (B), Top view of a wild-type Arabidopsis inflorescence, illustrating the indeterminacy of the shoot meristem. Panels (C)–(E) show 35S::LFY plants (generated in the Nossen ecotype), three weeks old. Panel (C), Replacement of shoots with single flowers (triangles) (line 151.201). A cotyledon is indicated (cot). Panel (D), Development of a primary terminal flower (1°) on the main shoot, and development of single secondary flower (2°) in the axil of a cauline leaf (cl). Single terminal flowers arising from the axils of curled rosette leaves (rl) are indicated by triangles (fine 151.209). Panel (E), Close-up view of primary and secondary flower shown in (D), at a different angle. The gynoecium (g), comprising the carpels, appears largely normal. The number of stamens (st) is reduced, and petals and sepals are absent. A single first-whorl organ with leaf-, sepal- and carpel-like features is indicated by an asterisk.

FIGS. 7A–7D show 35S::LFY phenotype is partly suppressed by an ap1 mutation. Panel a shows five-week-old plants that carry the erecta mutation. The 35S::LFY AP1$^+$ plant (left) has no elongated primary shoot. A primary shoot is well developed in the 35S::LFY ap1 plant (middle), although the primary shoot still terminates prematurely, and is shorter than that of the non-transgenic ap1 plant (right). Panels b-d show a detailed view of 35S::LFY ap1 plants. Panel b shows a close-up view of lateral shoot indicated by arrowhead in panel a. Panel c shows emerging shoots in the axils of rosette leaves. Panel d shows a top view of primary shoot with terminal flower (tf). Panels c and d are from a four-week-old plant. The ap1 effects are enhanced further by the cal-1 mutation, although there is no qualitative change in the 35S::LFY ap1 phenotype.

DETAILED DESCRIPTION OF THE INVENTION

Figure 1:
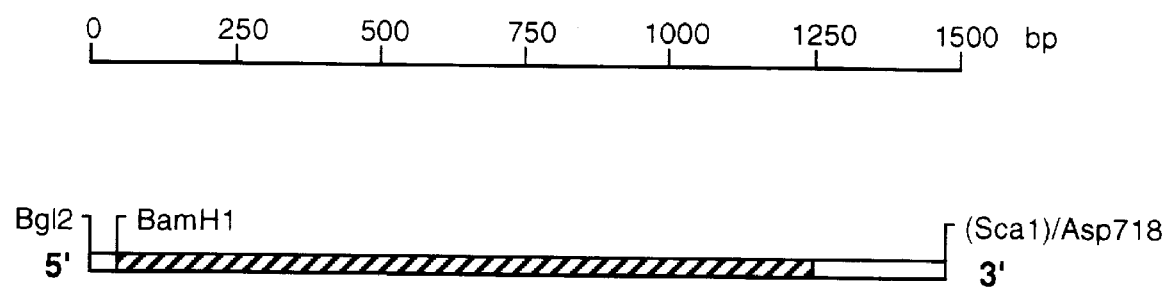
FIG. 1 shows a schematic illustration of pDW139, which is the parental plasmid for construction of 35S::LFY vectors. Open reading frame of LEAFY (LFY) is hatched; 5' and 3' untranslated regions are stippled.

The present invention provides a genetically modified plant which is characterized as having the phenotypic trait of early flower development, or early flowering. The plant is genetically modified by at least one structural gene that encodes a protein, such as LEAFY, which is sufficient to induce flowering in the plant.

In a first embodiment, the invention provides a genetically modified plant comprising at least one heterologous nucleic acid sequence in its genome and characterized as having modulated flower meristem development. Also included herein are plant cells and plant tissue, all derived from the genetically modified plant of the invention. In addition, seeds which can germinate into a genetically modified plant as described herein are also provided.

The term "genetic modification" as used herein refers to the introduction of one or more heterologous nucleic acid sequences into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any flowering plants amenable to transformation techniques, including both monocotyledonous and dicotyledonous plants.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Exemplary models described herein include the tobacco plant and the perennial tree, aspen.

The term "heterologous nucleic acid sequence" as used herein refers to at least one structural gene operably associated with a regulatory sequence such as a promoter. The nucleic acid sequence originates in a foreign species, or, in the same species if substantially modified from its original form. For example, the term "heterologous nucleic acid sequence" includes a nucleic acid originating in the same species, where such sequence is operably linked to a promoter that differs from the natural or wild-type promoter.

As used herein, the term "nucleic acid sequence" refers to a polymer of deoxyribonucleotides or ribonucleotides, in the form of a separate fragment or as a component of a larger construct. DNA encoding the proteins utilized in the method of the invention can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences.

Examples of structural genes that may be employed in the present invention include the LEAFY gene and the APETALA1 gene which control flowering. Also included in the present invention are structural and functional homologues of the LEAFY and APETALA1 genes. For example, in *Antirrhinum majus*, the snapdragon, the homologue of the LEAFY gene is the FLORICAULA gene and the homologue of the APETALA1 gene is the SQUAMOSA gene. Other genes which control flowering will be known to those of skill in the art or can be readily ascertained.

Nucleic acid sequences utilized in the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). Sequences for specific genes can also be found in GenBank, National Institutes of Health computer database.

Hybridization procedures useful for screening for desired nucleic acid sequences utilized herein employ labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

Specific DNA sequences encoding a heterologous protein of interest, such as LEAFY protein, can also be obtained by: 1) isolation of double-stranded DNA sequences from the genomic DNA; 2) chemical synthesis of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

A cDNA expression library, such as lambda gt11, can be screened indirectly for a heterologous polypeptide having at least one epitope, using antibodies specific for the heterologous protein. Such antibodies can be either polyclonally or monoclonally derived and used to detect expression product indicative of the presence of heterologous protein cDNA.

A polypeptide sequence can be deduced from the genetic code, however, the degeneracy of the code must be taken into account. Nucleic acid sequences utilized in the invention include sequences which are degenerate as a result of the genetic code. There are 20 natural amino acids, most of which are specified by more than one codon. Therefore, as long as the amino acid sequence of heterologous polypeptide results in a functional polypeptide (at least, in the case of the sense polynucleotide strand), all degenerate nucleotide sequences are included in the invention.

"Modulated" flower meristem development as used herein, refers to flower development in the plant which may be either accelerated or inhibited/delayed as compared to the naturally occurring, umnanipulated plant. Therefore, the term "modulate" envisions the acceleration or augmentation of flower development when development is desirable or suppression or inhibition of flower development when development is not desirable.

The heterologous nucleic acid sequences utilized herein are structural genes for flower meristem development. Preferably, such genes encode a protein that is sufficient for the initiation of flowering, and most preferably, the nucleic acid sequence encodes the LEAFY protein. The LEAFY gene or other flower meristem development gene may be utilized alone or in combination with another structural gene, such as another gene which encodes a protein important in the development of flowering. An example of such a gene is the APETALA1 gene.

Genetically modified plants of the present are produced by contacting a plant cell with a vector comprising a heterologous nucleic acid sequence comprising at least one structural gene encoding a protein that modulates flower meristem development. To be effective once introduced into plant cells, the structural gene of interest must be operably associated with a promoter which is effective in the plant cells to cause transcription of the gene of interest. Additionally, a polyadenylation sequence or transcription control sequence, also recognized in plant cells may also be employed. It is preferred that the vector harboring the heterologous nucleic acid sequence also contain one or more selectable marker genes so that the transformed cells can be selected from non-transformed cells in culture, as described herein.

The term "operably associated" refers to functional linkage between a promoter sequence and the structural gene regulated by the promoter nucleic acid sequence. The operably linked promoter controls the expression of the polypeptide encoded by the structural gene.

The expression of structural genes employed in the present invention may be driven by a number of promoters. Although the endogenous promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., *Nature,* 310:511, 1984; Odell, et al., *Nature,* 313:810, 1985); the full-length transcript promoter from Figwort Mosaic Virs FMV) (Gowda, et al., *J Cell Biochem.,* 13D: 301, 1989) and the coat protein promoter to TMV (Takamatsu, et al., *EMBO J* 6:307, 1987). Alternatively, plant promoters such as the light-inducible promoter from the small subunit of ribulose bis-phosphate carboxylase (ssRUBISCO) (Coruzzi, et al., *EMBO J,* 3:1671, 1984; Broglie, et al., *Science,* 224:838, 1984); mannopine synthase promoter (Velten, et al., *EMBO J,* 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hspl7.3-B (Gurley, et al., *Mol. Cell. Biol.,* 6:559, 1986; Severin, et al., *Plant Mol. Biol.,* 15:827, 1990) may be used.

Promoters useful in the invention include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.,* 90:4567, 1993); In2-1 and In2-2 regulator sequences which are activated by substituted benzenesulfonamides, e.g., herbicide safeners (Hershey, et al., *Plant Mol. Biol,* 17:679, 1991); and the GRE regulatory sequences which are induced by glucocorticoids (Schena, et al., *Proc. Natl. Acad Sci., USA.,* 88:10421, 1991). Other promoters, both constitutive and inducible and enhancers will be known to those of skill in the art.

The particular promoter selected should be capable of causing sufficient expression to result in the production of an effective amount of the structural gene product, e.g., LEAFY, to cause early floral meristem development. The promoters used in the vector constructs of the present invention may be modified, if desired, to affect their control characteristics.

Tissue specific promoters may also be utilized in the present invention. An example of a tissue specific promoter is the promoter expressed in shoot meristems (Atanassova, et al., *Plant J.,* 2:291, 1992). Other tissue specific promoters useful in transgenic plants, including the cdc2a promoter and cyc07 promoter, will be known to those of skill in the art. (See for example, Ito, et al., *Plant Mol. Biol.,* 24:863, 1994; Martinez, et al., *Proc. Natl. Acad Sci. USA,* 89:7360, 1992; Medford, et al., *Plant Cell,* 3:359, 1991; Terada, et al., *Plant Journal,* 3:241, 1993; Wissenbach, et al., *Plant Journal,* 4:411, 1993).

Optionally, a selectable marker may be associated with the heterologous nucleic acid sequence, ie., the structural gene operably linked to a promoter. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phosphoribosyl-transferase and amino-glycoside 3'-O-phosphotransferase II (kanamycin, neomycin and G418 resistance). Other suitable markers will be known to those of skill in the art.

Vector(s) employed in the present invention for transformation of a plant cell to modulate flower meristem development comprise a nucleic acid sequence comprising at least one structural gene encoding a protein that modulates flower meristem development, operably associated with a promoter. To commence a transformation process in accordance with the present invention, it is first necessary to construct a suitable vector and properly introduce it into the plant cell. The details of the construction of the vectors then utilized herein are known to those skilled in the art of plant genetic engineering.

For example, the heterologous nucleic acid sequences utilized in the present invention can be introduced into plant cells using Ti plasmids, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., *Science,* 227:1229, 1985, both incorporated herein by reference).

One of skill in the art will be able to select an appropriate vector for introducing the heterologous nucleic acid sequence in a relatively intact state. Thus, any vector which will produce a plant carrying the introduced DNA sequence should be sufficient. Even a naked piece of DNA would be expected to be able to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of a heterologous nucleic acid sequence.

For example, a heterologous nucleic acid sequence can be introduced into a plant cell utilizing *Agrobacterium tumefaciens* containing the Ti plasmid. In using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology,* 1:262, 1983; Hoekema, et al., *Nature,* 303:179, 1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacterium; or 3) transformation of seeds, apices or meristems with Agrobacterium. In addition, gene transfer can be accomplished by in situ transformation by Agrobacterium, as described by Bechtold, et al., (*C. R. Acad. Sci. Paris,* 316:1194, 1993) and exemplified in the Examples herein. This approach is based on the vacuum infiltration of a suspension of Agrobacterium cells.

The preferred method of introducing heterologous nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants. A preferred vector(s) of the invention comprises a Ti plasmid binary system wherein the heterologous nucleic acid sequence encodes the LEAFY protein. Such a vector may optionally contain a nucleic acid sequence which encodes a second flower development factor, such as APETALA1. Alternatively, two vectors can be utilized wherein each vector contains a heterologous nucleic acid sequence. Other flower development genes can be utilized for construction of one or more vectors, in a similar manner.

Alternatively, heterologous nucleic acid can be introduced into a plant cell by contacting the plant cell using mechanical or chemical means. For example, the nucleic acid can be mechanically transferred by microinjection directly into plant cells by use of micropipettes. Alternatively, the nucleic acid may be transferred into the plant cell by using polyethylene glycol which forms a precipitation complex with genetic material that is taken up by the cell.

Heterologous nucleic acid can also be introduced into plant cells by electroporation (Fromm, et al., *Proc. Natl. Acad Sci., U.S.A.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., *Nature* 327:70, 1987). Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

In another embodiment, the invention includes a method of producing a genetically modified plant characterized as having modulated flower meristem development, said method comprising contacting a plant cell with a vector, comprising a heterologous nucleic acid sequence comprising at least one structural gene encoding a protein for modulating flower meristem development, operably associated with a promoter to obtain a transformed plant cell; growing a plant from said transformed plant cell; and selecting a plant exhibiting modulated flower meristem development.

As used herein, the term "contacting" refers to any means of introducing the vector(s) into the plant cell, including chemical and physical means as described above. Preferably, contacting refers to introducing the nucleic acid or vector into plant cells (including an explant, a meristem or a seed), via *Agrobacterium tumefaciens* transformed with the heterologous nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxin and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology,* Vol. 118 and Klee, et al., *Annual Review of Plant Physiology,* 38:467, 1987). Utilizing the leaf disk-transformation-regeneration method of Horsch, et al., *Science,* 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The inbred plant produces seed containing the newly introduced foreign gene(s). These seeds can be grown to produce plants that would produce the selected phenotype, e.g. early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting modulated flower meristem development can be selected by visual observation. The invention includes a plant produced by the method of the invention, including plant tissue, seeds, and other plant cells derived from the genetically modified plant.

In yet another embodiment, the invention provides a method for modulating flower meristem development in a plant cell, said method comprising contacting said plant cell with a vector as described above to obtain a transformed plant cell, growing the transformed plant cell under plant forming conditions, and modulating flower meristem development in the plant. The method of the invention requires that the promoter sequence operably linked with the structural gene. The promoter is an inducible promoter when induction of flower development is desired. For example, a plant cell and plant is produced as described above and modulated flower meristem development is induced by contacting the promoter, linked with a nucleic acid sequence encoding LEAFY, with an appropriate inducer. Such inducible promoters are described above, and include those promoters preferably inducible by chemical means.

While the present examples demonstrate that constitutive expression of a floral regulatory gene (LEAFY) causes accelerated flowering, this system could be modified such that flowering would be inhibited. For example, dominant-negative versions of floral regulatory genes could be expressed constitutively. Dominant-negative mutants are proteins that actively interfere with the function of a normal, endogenous protein. Thus, the action of a gene can be blocked without inactivating the structural gene itself or its RNA. This strategy has been successful for transcription factors (e.g., Attardi, et al., *Proc. Natl. Acad Sci. USA*, 90:10563, 1993; Lloyd, et al., *Nature*, 352:635, 1991; Logeat, et al., *EMBO J.*, 10:1827, 1991: Mantovani, et al., *J. Biol. Chem.*, 269:20340, 1994; Ransone, et al., *Proc. Natl. Acad. Sci. USA*, 87:3806, 1990; Richardson, et al., *Mech. Dev.*, 45:173, 1994; Tsai, et al., *Genes Dev.*, 6:2258, 1992.) The LEAFY protein is likely to be a transcription factor, as it localizes to the nucleus and can bind to DNA in vitro. Likewise, most other floral regulatory genes, including APETALA1, encode known transcription factors with a MADS DNA-binding domain (e.g., Mandel, et al., *Nature*, 360:273, 1992).

The above disclosure generally describes the present invention. A more complete understanding can be obtained by reference to the following specific examples which are provided herein for purposes of illustration only and are not intended to limit the scope of the invention.

EXAMPLES

To study the effects of ectopic LEAFY (LFY) expression, a chimeric gene in which the LFY coding region is under the control of the constitutive 35S promoter from cauliflower mosaic virus (CaMV) was constructed (Odell, J. T., et al. *Nature*, 313:810, 1985.) By way of illustration, the chimeric 35S::LFY gene was introduced into Arabidopsis and the distantly related tobacco plants by T-DNA mediated transformation. Other examples show aspen trees transformed with LFY. The phenotypic effects observed in transgenic plants show that LFY is not only necessary, but also sufficient for the initiation of flower development.

EXAMPLE 1

CONSTRUCTION OF TRANSFORMATION VECTORS

For transformation of tobacco, the pDW146 vector was used. For transformation of Arabidopsis, the pDW151 vector was used. Both vectors are derived from plasmid pDW139, which contains the entire open reading frame of the LEAFY (LFY) gene from *Arabidopsis thaliana* (Weigel, D., et al., *Cell*, 69:843, 1992), plus 21 bp upstream of the initiation codon and 195 bp downstream of the stop codon (for cDNA sequence, see Weigel et al., supra; genomic sequence deposited in GenBank under accession number M91208). At the 5' end, a Bgl2 site was added by polymerase chain reaction (Saiki, et al., *Science*, 239:487, 1988). At the 3' end, a genomic ScaI site was eliminated in the cloning process, and it is followed immediately by an Asp718 site derived from the pBluescript KS+ cloning vector (FIG. 1).

FIG. 1 shows a schematic illustration of pDW139 parental plasmid for construction of 35S::LFY vectors. The open reading frame of LEAFY (LFY) is hatched; 5' and 3' untranslated regions are stippled.

To construct pDW146, the 1.5 kb Bgl2/Asp718 fragment carrying the LFY sequences was inserted into the binary T-DNA transformation vector pMON530 (Rogers, et al., *Meth. Enzymol*, 153:253, 1987), using the same sites in the vector. This vector contains an expression cassette comprising a 0.3 kb fragment of the cauliflower mosaic virus 35S promoter, including the transcription initiation site (Guilley, et al., *Cell*, 30:763, 1982); Odell, et al, supra.); a multilinker containing several unique restriction sites; and a functional polyadenylation signal from the Ti plasmid T-DNA nopaline synthase gene ("3' nos"; [Bevan, et al., *Plant Cell*, 1:141, 1983]).

To construct pDW151, the Asp718 site of pDW139 was filled in with Klenow enzyme (Sambrook, et al., *Molecular Cloning 2nd ed.* (Cold Spring Harbor: Cold Spring Harbor Laboratory, 1989) and a Bg linker was added. The resulting Bgl2 fragment was inserted into the BamHl site of pCGN18, a transformation vector containing a CaMV 35S promoter 3' nos expression cassette (Jack, et al., *Cell*, 76:703, 1994).

pDW146 and pDW151 plasmid DNAs isolated from *E. coli* were transformed into *Agrobacterium tumefaciens* strain LBA4404 (Ooms, et al., *Plasmid*, 7:15, 1982) or ASE (Fraley, et al., *Biotechnology* 3:629, 1985), respectively, using the freeze-thaw method as described (Höfgen and Willmitzer, *Nucl. Acids Res.*, 16:9877, 1988), except that LB medium (Sambrook, et al., supra) was used instead of YEB.

EXAMPLE 2

GENERATION OF TRANSGENIC TOBACCO PLANTS

For generation of transgenic tobacco plants, leaf pieces of sterily grown tobacco strain *Nicotiana tabacum* var. Xanthi were infected with LBA4404/pDW146, and plants were regenerated as described (Horsch, et al., *Science*, 227:1229, 1985). Selection for transformed plants was with 200 µg/ml kanamycin. Kanamycin resistant regenerated plants were transferred to soil, and seeds were harvested from the primary transformants.

Figure 2:
FIG. 2 shows the early flowering phenotype of 35S::LFY tobacco plants. Left, control plant, transformed with an unrelated construct. Middle and right, two independently derived $T_2$ plants carrying a 35S::LFY transgene (lines 146.21, 146.26). Plants are five weeks old.

FIG. 2 shows the early flowering phenotype of 35S::LFY tobacco plants. The left panel shows a control plant, transformed with an unrelated construct (a LFY promoter fused to a GUS reporter gene). The middle and right panels show two independently derived $T_2$ plants carrying a 35S::LFY transgene (lines 146.21, 146.26). The plants shown are five weeks old. Note abundant proliferation of leaves in the control, while the experimental plants have produced only two true leaves before initiating a terminal flower. The insert shows a top view of floral bud of plant shown at the right. The bud is still unopened.

Figures 3A, 3B:
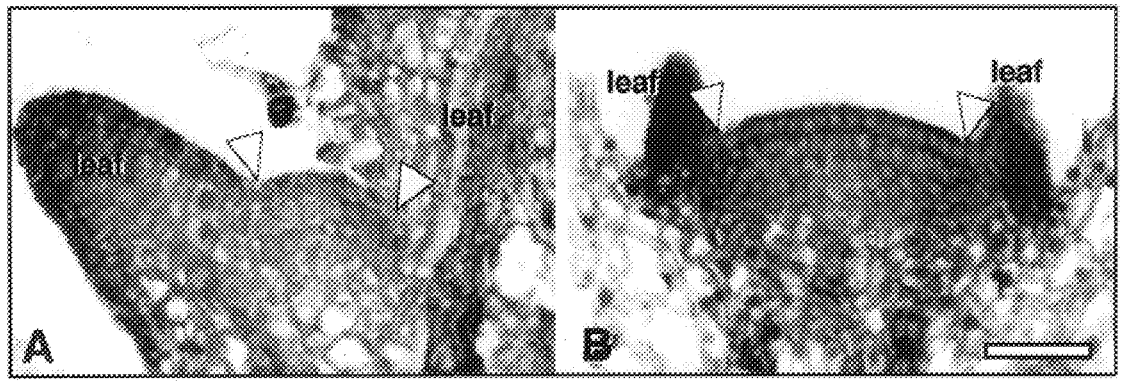
FIGS. 3A–3B show precocious enlargement of apical meristem in 35S::LFY tobacco plants. Panel (A), Control, transformed with an unrelated construct. Panel (B), Experimental plant, transformed with a 35S::LFY construct. Size bar, 50 μm.

Of 32 transgenic tobacco lines analyzed in detail, 27 exhibit the same dramatic phenotype in the progeny of the primary transformants ($T_2$ generation). Transgenic plants develop only one pair of true leaves, in addition to the embryonic leaves (cotyledons), before they produce a terminal flower (FIG. 2). Although wild-type tobacco plants also produce a terminal flower, they generate twenty to twenty-five pairs of leaves before flowering. Thus, constitutive LFY expression causes precocious conversion of the shoot meristem into a floral meristem. Histological sections of transgenic plants reveal that the apical meristem is morphologically different from that of untransformed plants at least as early as five days after germination (FIG. 3). The result of these changes is that transformed plants produce visible floral buds after two weeks, while normal tobacco plants flower only after about three to five months (the exact time depends on environmental conditions, such as light intensity, fertilizer, size of pots in which plants are grown, etc.).

FIG. 3 shows precocious enlargement of apical meristem in 35S::LFY tobacco plants. Panel (A) is a control, transformed with the unrelated construct described in FIG. 2. Panel (B) shows an experimental plant, transformed with a 35S::LFY construct. Plants were sacrificed five days after germination, fixed, embedded in paraffin, and sectioned. Triangles indicate width of meristems. Note that the leaf primordia arising at the flanks of the 35S::LFY meristem are retarded compared to those on the control meristem. Size bar, 50 µm.

The precocious flowers of 35 S::LFY tobacco plants are abnormal in organ identity and organ number. The floral buds are surrounded by small leaf-like organs, and petals are either absent or sepaloid. Stamens and carpels are morphological normal, but their number deviates from wild-type, being in most cases higher. Neither second-order shoots nor flowers develop from the axils of the two true leaves, although adventitious shoots can arise from the hypocotyl.

EXAMPLE 3

GENERATION OF TRANSGENIC ARABIDOPSIS PLANTS pDW151 was introduced into Arabidopsis by vacuum infiltration (Bechtold, et al., *C.R. Acad Sci.,* 316:1194, 1993). Leaves of adult *Arabidopsis thaliana* plants of the ecotypes Wassilewskija (Ws-0) and Nossen (No-0) were infiltrated with ASE/pDW151, and seeds were harvested from the infiltrated plants. Seeds were grown on MS medium (Murashige and Skoog, *Physiol. Plant,* 15:473, 1962) supplemented with 50 µg/ml kanamycin. Transformed plants were identified by their ability to grow on kanamycin containing medium. Using this method, 27 transgenic 35S::LFY Arabidopsis plants were isolated, of which 21 exhibited essentially the same dramatic phenotype, which was very similar to that observed in 35S::LFY tobacco plants.

The transformation experiment utilized a new method that circumvents tissue culture and regeneration of plants from callus, and allows directly for the generation of transgenic seeds (Bechtold, et al., *C.R. Acad Sci.,* 316:1194, 1993). In this method, leaves of adult plants are vacuum-infiltrated with a suspension of Agrobacterium cells carrying a T-DNA plasmid. The Agrobacterium cells grow in planta, where they transfer their T-DNA to host cells, including the precursors of gamete producing cells. Seeds were harvested from the infiltrated plants, and grown on antibiotic containing medium to select for transformants. A small fraction of seeds, between one in several hundred to one in several thousand, were stably transformed with the T-DNA. (A single Arabidopsis plant can produce several thousand seeds.)

The following description of the 35S::LFY phenotype in Arabidopsis is based on the analysis of first generation transformants. The phenotype should not change significantly in subsequent generations, because these transformants have been grown from seeds, as opposed to having been regenerated from tissue culture. The same method has been used to generate transformants with four other constructs, none of which cause the phenotype observed with the 35S::LFY construct.

FIG. 4 shows the early flowering phenotype of 35S::LFY Arabidopsis plants. In panel (A), a control plant, transformed with an unrelated construct. The rosette leaves (rl) are significantly larger than the cotyledons (cot). Panel (B) shows a 35 S::LFY transformant (line 151.106). The first two rosette leaves (rl) are smaller than the cotyledons. A tiny shoot has formed, with what appear to be two cauline leaves (cl). The floral bud is still unopened. Both plants, which are 17 days old, were selected on kanamycin containing medium for a week, which is likely to have slowed their development somewhat.

FIG. 5 shows the conversion of all shoots into flowers in 3 5 S::LFY Arabidopsis plants. Panel (A) shows a drawing of a mature Arabidopsis plant (Nossen ecotype) of about six weeks of age. Note that indeterminate shoots develop from the axils of all rosette and stem leaves. These shoots bear a few leaves themselves, before they start to produce flowers. Panel (B) shows a top view of a wild-type Arabidopsis inflorescence, illustrating the indeterminacy of the shoot meristem. Flowers develop in a phyllotactic spiral, with the youngest flowers being the closest to the center. Panels (C)-(E), 35S::LFY plants (generated in the Nossen ecotype), three weeks old. Panel (C), Replacement shoots with single flowers (triangles) (line 151.201). A cotyledon is indicated (cot). Panel (D), Development of a primary terminal flower (1°) on the main shoot, and development of single secondary flower (2°) in the axil of a cauline leaf (cl). Single terminal flowers arising from the axils of curled rosette leaves (rl) are indicated by triangles (line 151.209). Panel (E), Close-up view of primary and secondary flower shown in (D), at a different angle. Note that the primary terminal flower is abnormal. The gynoecium (g), comprising the carpels, appears largely normal. The number of stamens (st) is reduced, and petals and sepals are absent. A single first-whorl organ with leaf-, sepal- and carpel-like features is indicated by an asterisk.

Figures 4A, 4B:
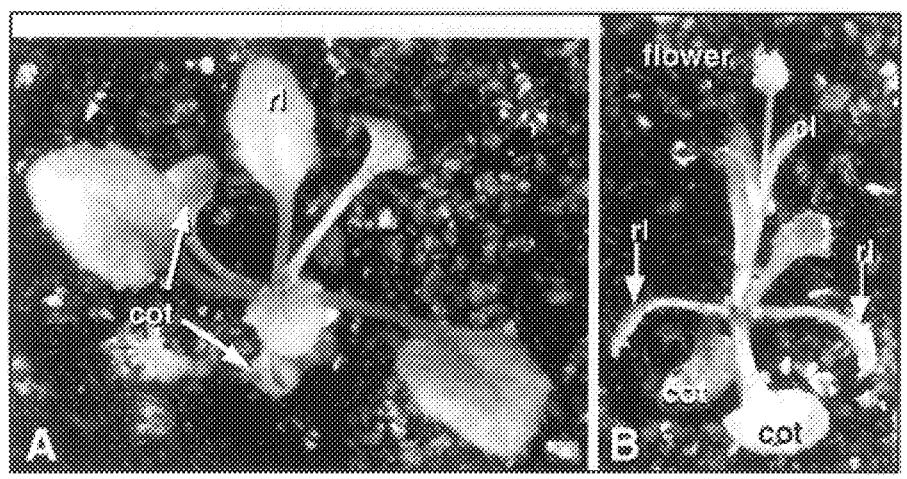
FIGS. 4A–4B show the early flowering phenotype of 35S::LFY Arabidopsis plants. Panel (A), Control plant, transformed with an unrelated construct. The rosette leaves (rl) are significantly larger than the cotyledons (cot). Panel (B), 35S::LFY transformant (line 151.106). The first two rosette leaves (rl) are smaller than the cotyledons. A small shoot has formed, with what appear to be two cauline (=stem) leaves (cl).

35S::LFY Arabidopsis plants flower earlier than wild-type plants. There are only two to five rosette leaves, compared to at least eight in wild-type plants, and a stage 12 floral bud can be visible as early as 17 days after germination (FIG. 4). Since it takes two weeks for the development of a stage 12 flower (Smyth, et al., *Plant Cell,* 2:755, 1990), flowers must initiate within a few days after germination. This is much earlier than in wild type, where the first flowers are initiated only when a plant is about two weeks old. Unlike tobacco, Arabidopsis has an open inflorescence, meaning that the shoot apical meristem remains undifferentiated until the plant dies. The 35S::LFY plants not only flower earlier, but their primary axis terminates with a single flower, similar to the tfl mutant phenotype (see FIG. 1). Thus, ectopic expression of LFY causes transformation of the indeterminate shoot meristem into a determinate floral meristem. In contrast with the tfl mutant phenotype, no normal lateral flowers are formed before the primary terminal flower develops (FIGS. 4B and 5D). Additional terminal flowers develop from the axils of leaves in 35S::LFY plants, indicating a transformation of second-order shoot meristems as well (FIGS. 5C and 5D). Surprisingly, most 35S: :LFY plants develop a tiny shoot, with one or two leaves that resemble cauline (stem) leaves of wild type (FIGS. 4B and 5D). For comparison, FIG. 5A illustrates the normal architecture of a mature Arabidopsis plant, with indeterminate shoots arising from the axils of all leaves.

The early flowering phenotype, and the transformation of a shoot into a floral meristem, show that LFY activity is sufficient to determine the identity of a meristem. However, since the shoot meristem produces leaves before it is converted into a floral meristem, there appear to be additional factors that prevent the shoot meristem from responding to LFY activity immediately after germination.

35S:LFY plants appear to flower faster than any other early flowering mutant that has been described in Arabidopsis, including the embryonic flower (emf) mutant, which appears to skip the rosette phase of vegetative development (Sung, et al., *Science*, 258:1645–1647, 1992). Unfortunately, the exact time of flower initiation in emf mutants has not been reported, but the data presented by Sung, et al., supra indicate that flower primordia are not formed before the plant is at least nine days old, making the emf phenotype distinct from the 35S::LFY phenotype. It appears that emf mutants pause after germination, and then proceed directly to the formation of an inflorescence.

The exact phenotype of individual 35S::LFY Arabidopsis plants varies. Most flowers observed are virtually identical to wild-type flowers (FIGS. 5D and E). Very importantly, for further analysis, stamens and carpels are fertile. The primary terminal flowers are often abnormal, in that the outer organs are leaf-like or absent, and the numbers of petals is reduced, similar to the effect seen in the terminal flowers of 35S::LFY tobacco plants (FIG. 5E). In addition, carpels can be unfused, and the number of stamens can be lower than the wild-type number of six.

The finding that the LEAFY gene from Arabidopsis can modify flowering in tobacco implies that the mode of LEAFY function is well conserved among flowering plants, that the Arabidopsis gene is likely to function in a wide variety of flowering plants. Arabidopsis and tobacco belong to two very divergent subclasses among the class of dicotyledonous plants. Arabidopsis is a genus within the family Brassicaceae, which belongs to the order Capparales within the subclass Dilleniidae. Tobacco, *Nicotiana tabacum*, belongs to the family Solanaceae, within the order Solanales of the subclass Asteridae. The Dilleniidae are closely related to the Magnoliidae, the most primitive subclass of dicotyledonous plants. In contrast, the Asteridae are the most advanced subclass of dicotyledons (Cronquist, A., *An Integrated System of Classification of Flowering Plants*, 1981 (New York: Columbia University Press).

The two familes to which Arabidopsis and tobacco belong, Brassicaceae and Solanaceae, are large familes of major economic importance (Heywood, V. H., *Flowering Plants of the World*, 1993, (New York: Oxford University Press). Main crops within the Brassicaceae include oilseed rape and cabbage and its relatives, such as kale, cauliflower, broccoli, and Chinese cabbage. The family Solanaceae is one of the most important serving humankind, containing many essential vegetables and fruits such as potatoes, tomatoes, aubergines, paprika, chilies, and bell peppers.

Recent work has shown that close homologs of Arabidopsis floral regulatory genes exist in monocotyledonous plants. For example, homologs of the APETALA1 and LEAFY genes have been identified in maize (Veit, et al., *Plant Cell*, 5:1205, 1993; Weigel and Meyerowitz, In *Molecular Basis of Morphogenesis, pp.* 91–105, 1993, (New York: Wiley-Liss).

EXAMPLE 4

CONVERSION OF ASPEN SHOOTS

Because constitutive expression of LFY can induce flowers precociously during the vegetative phase of Arabidopsis, other species were examined as well. The effect of constitutive LFY expression was studied in a perennial tree, hybrid aspen, which is derived from parental species that flower naturally only after 8–20 years (Schreiner, E. J. in *USDA Agriculture Handbook*, 450: *Seeds of Woody Plants in the United States* (ed. Schopmeyer, C. S.) pp. 645–655 (U.S. Government Printing Office, Washington D.C., 1974). 35S::LFY aspen plants were obtained by Agrobacterium-mediated transformation of stem segments and subsequent regeneration of transgenic shoots in tissue culture (Nilsson, O., et al., *Transgen. Res.*, 1:209, 1992).

Hybrid aspen was transformed as described previously (Nilsson, O., et al., ibid). Levels of LFY RNA expression were similar to those of 35S::LFY Arabidopsis, as determined by Northern blot analysis. The number of vegetative leaves varied between the different regenerating shoots. Those with a higher number of vegetative leaves formed roots, allowing for transfer to the greenhouse. Individual flowers were removed either from primary transformants that had been transferred to the greenhouse, or from catkins collected in spring 1995 at Carlshem (Umea, Sweden) from a tree whose age was determined by counting the number of annual rings in a core extracted with an increment borer at 1.5 m above ground level. Flowers were fixed in formaldehyde/acetic acid/ethanol, and destained in ethanol before photography.

FIG. 6 shows that constitutive expression of Arabidopsis LFY converts aspen shoots into flowers. Panels a and b show five-month-old shoots of hybrid aspen (*Populous tremula* x *tremuloides*) grown in tissue culture. Panel a shows a 35S::LFY transformant. Solitary, lateral flowers in the axils of leaves (lf) and an abnormal terminal flower (tf) are indicated. Panel b shows a non-transgenic control. Arrowheads indicate axils of leaves, from which lateral vegetative shoots will emerge, normally in the following year. Note that aspen plants regenerated from tissue culture show the same juvenile phenotype during the first growing cycle as plants grown from seed (Nilsson, O., supra) Panel C is a close-up view of solitary male flower that formed in a leaf axil of a seven-month-old 35S::LFY transformant that had been transferred to the greenhouse. Panel d shows a close-up view of male flower removed from wild-type catkin shown in panel e. Note bract (b) subtending wild-type flower. Panel e shows a cluster of male catkins of *P. tremula*, one of the parental species of hybrid aspen, taken from a 15-year-old tree. Red pigment in anthers is apparent. Scale bars: a,b, 5 mm; c, d, 1 mm; e, 20 mm.

Figure 6A:
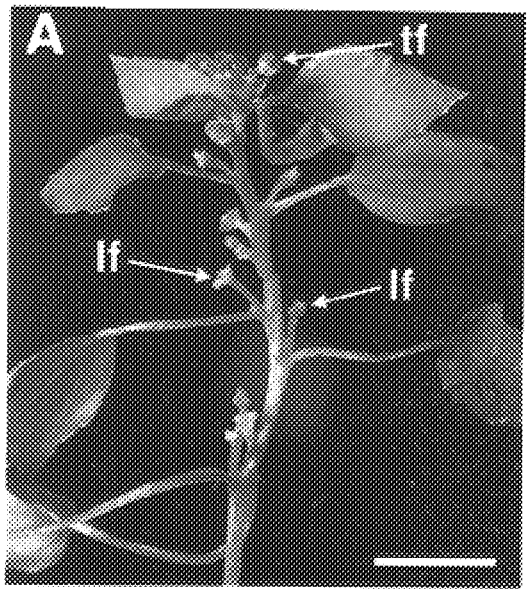
FIGS. 6A–6E show constitutive expression of Arabidopsis LFY converts aspen shoots into flowers. Panels a and b show five-month-old shoots of hybrid aspen (*Populous tremula* x tremuloides) grown in tissue culture. Panel a shows a 35S::LFY transformant. Solitary, lateral flowers in the axils of leaves (lf) and an abnormal terminal flower (tf) are indicated. Panel b shows a non-transgenic control. Arrowheads indicate axils of leaves, from which lateral vegetative shoots will emerge, normally in the following year. Note that aspen plants regenerated from tissue culture show the same juvenile phenotype during the first growing cycle as plants grown from seed (Nilsson, O., Thesis, *Swedish Univ. Agricul. Sciences,* 1995) Panel C is a close-up view of solitary male flower that formed in a leaf axil of a seven-month-old 35S::LFY transformant that had been transferred to the greenhouse. Panel d shows a close-up view of male flower removed from wild-type catkin shown in panel e. Note bract (b) subtending wild-type flower. Panel e shows a cluster of male catkins of *P. tremula,* one of the parental species of hybrid aspen, taken from a 15-year-old tree. Red pigment in anthers is apparent. Scale bars: a,b, 5 mm; c, d, 1 mm; e, 20 mm.
Figure 6B:
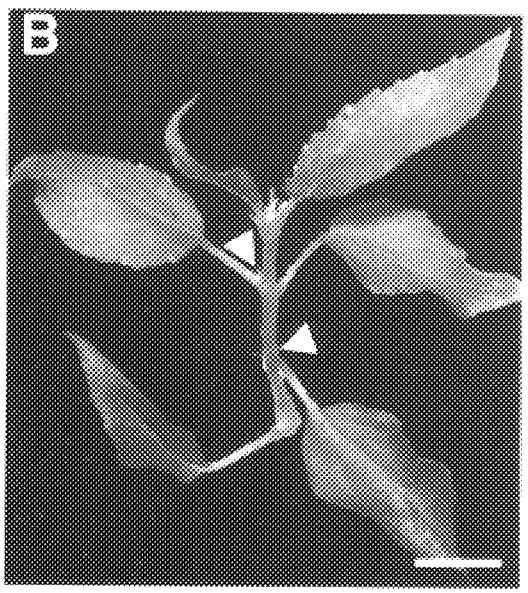
Figure 6C:
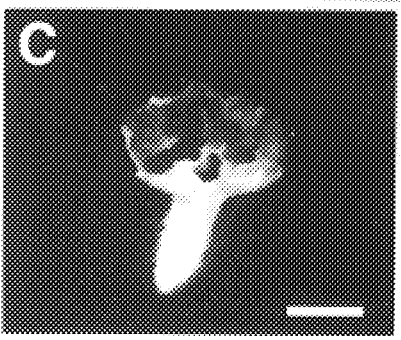

Regenerating 35S::LFY aspen shoots initially produced solitary flowers in the axils of normal leaves (FIG. 6a,e). However, the number of vegetative leaves is limited, and the shoot meristem is prematurely consumed in the formation of an aberrant terminal flower (FIG. 6a). Precocious flower development is specific to 35S::LFY transformants, as such an effect was not observed in non-transgenic controls (FIG. 6b). Furthermore, not a single instance of precocious flower development has been seen in the more than 1,500 other lines of transgenic aspen that were generated with various constructs during the past six years at the Swedish University of Agricultural Sciences (Nilsson O., et al., 1992 supra; Nilsson, O. Thesis, *Swedish University of Agricultural Sciences*, 1995).

Figure 6D:
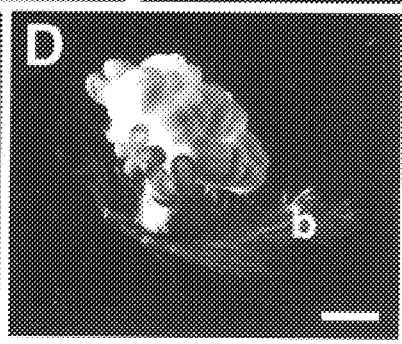
Figure 6E:
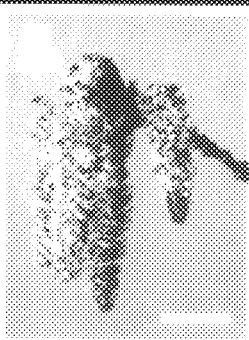

Although wild-type Arabidopsis and aspen are rather different, one being a weed and the other a tree, the overall phenotype of 35S: :LFY aspen very much resembles that of 35S::LFY Arabidopsis. In wild-type plants of both species, flowers are normally formed in lateral positions on inflorescence shoots. In aspen, these inflorescence shoots are called catkins and arise from the leaf axils of adult trees (FIG. 6d, e). In both 35S::LFY Arabidopsis and 35S::LFY aspen, solitary flowers form instead of shoots in the axils of vegetative leaves. Moreover, as in Arabidopsis, the secondary shoots of trangenic aspen are more severely affected than the primary shoot.

An apparent LFY orthologue from poplar has been described (Strauss, S. H., et al., *Mole. Breed*, 1:5, 1995) which, similarly to tobacco LFY (Kelly, A., et al., PL Cell, 7:225, 1995) is already expressed during the vegetative stage. The vegetative expression might have suggested that LFY activity is not sufficient to induce flower development in these species. The present results in aspen, which is the same in genus as poplar, indicate that this is not the case, a finding that extends to tobacco, which also flowers very early when transformed with a 35S:: Arabidopsis LFY construct (see Examples 1–3). One possible explanation for the effects of 35S::LFY in these species is that the transgene is expressed at higher effective levels in than the endogenous gene. In tobacco, expression of the endogenous gene in the center of the shoot meristem (which eventually turns into a flower meristem and forms a terminal flower) is relatively low (Kelly, A. J., et al., supra.), and it is conceivable that the other genes, such as AP1, are the primary regulators of flower-meristem-identity in non-transgenic tobacco.

EXAMPLE 5

MEDIATION OF LEAFY ACTIVITY BY APETALA1

In addition to LFY, mutations in the genes AP1, CAL, APETALA2 (AP2) and UNUSUAL FLORAL ORGANS (UFO) are known to affect the identity of Arabidopsis flower meristems Handel, M. A., et al., *Nature*, 360:273, 1992; Irish, V. F. & Sussex, I. M., *Pl. Cell*, 2:741, 1990; Jofuku, K. D., et al., *Pl. Cell*, 6, 1994; Levin, J. Z. & Meyerowitz, E. M. *Pl. Cell*, 7:529, 1995) although lfy mutations have generally the strongest effects, and are the only ones that consistently cause a complete transformation of at least a few flowers into shoots. Mutations in all five genes also affect the identity of floral organs, but meristem-identity and organ-identity defects are at least in some cases separable (Bowman, J. L., et al., *Development*, 119:721, 1993; Jack, T., et al., *Cell*, 76:703, 1994). To determine whether any of the other genes are required to mediate the effects of 35S::LFY on meristem identity, or whether their inactivation would merely affect the identity of floral organs in 35S::LFY flowers, the 35S::LFY transgene was crossed into various mutant backgrounds.

A 35S::LFY tranformant (line DW151.117, Wassilewskija ecotype) was crossed to ap1-1 (Landberg erecta ecotype) (Irish, F. V. & Sussex, I. M., *PI Cell* 2:741, 1990.). Transheterozygote $F_1$ progeny was either backcrossed to ap1-1 or allowed to self-fertilize. The cal genotype of selfed $F_2$ progeny was determined by polymerase chain reaction (PCR)(Kempin, S. A., et al., *Science*, 267:552, 1994).

FIG. 7 shows that 35S::LFY phenotype is partly suppressed by an ap1 mutation. Panel a shows five-week-old plants that carry the erecta mutation. The 35S::LFY AP1$^+$ plant (left) has no elongated primary shoot. A primary shoot is well developed in the 35S::LFY ap1 plant (middle), although the primary shoot still terminates prematurely, and is shorter than that of the non-transgenic ap1 plant (right). Panels b–d show a detailed view of 35S::LFY ap1 plants. Panel b shows a close-up view of lateral shoot indicated by arrowhead in panel a. Panel c shows emerging shoots in the axils of rosette leaves. Panel d shows a top view of primary shoot with terminal flower (tf). Panels c and d are from a four-week-old plant. The ap1 effects are enhanced further by the cal-1 mutation, although there is no qualitative change in the 35S: :LFY ap1 phenotype.

The ap2-1, ap2-2 and ufo-2 mutations caused only additive phenotypes, and did not significantly affect the shoot-to-flower conversion in 35S: LFY plants. In contrast, the ap1-1 mutation suppressed the 35S: :LFY phenotype to a notable extent, although terminal flowers were still formed (FIG. 7). Both the primary and secondary shoots were affected, with the strongest effects being observed in lateral positions (FIG. 7b,c). The solitary flowers that develop in the axils of rosette leaves of 35S::LFY AP1$^+$ plants become complex shoots with an average of 10 nodes in 35S::LFY ap1 plants (FIG. 7c). These observations not only confirmed that LFY can induce AP1 (which fails to become activated in early arising flowers of lfy mutants), but also that the combined activities of LFY and AP1 are ever more effective in transforming shoot meristems into flower meristems than LFY activity alone.

Taken together, these results suggest that competence to respond to flower-meristem-identity genes is acquired gradually. In young meristems, competence appears to be low, and both LFY and AP1 are required to promote flower development over that of shoots. Competence increases later in the life cycle, and LFY alone becomes sufficient to induce flower development.

SUMMARY

The present invention shows that constitutive expression of a single flower meristem identity gene, such as LEY or AP1, can induce precocious flower development in plants as diverse as Arabidopsis, an ephermeral weed, and aspen, a perennial tree. The results not only contribute to the understanding of flower development and floral induction, they are also likely to be of interest because shorter flowering times lead to shorter generation times, which in turn allows acceleration of breeding programs. Modem crop varieties are the result of continued improvement by breeding and two recently developed technologies have made breeding even more important. The first technology is molecular mapping, with which genes encoding desirable traits can be rapidly located within the genome. Introduction of such traits into agriculturally important varieties is now greatly assisted by monitoring linked molecular markers, instead of testing for actual expression of these traits. The second technology is transformation of plants with hybrid genes conferring various traits such as engineered pathogen resistance. However, progress in this area has been delayed because the number of plant varieties amenable to transformation is often restricted, and extensive backcrossing is needed to introgress transgenes into a desired background. In both cases, marker-assisted breeding and transgene introgression, reduction of generation time through the induction of precocious flowering should prove useful.

The foregoing is meant to illustrate, but not to limit, the scope of the invention. Indeed, those of ordinary skill in the art can readily envision and produce further embodiments, based on the teachings herein, without undue experimentation.

I claim:

1. A genetically modified plant having in its genome a heterologous nucleic acid sequence encoding a flower meristem identity protein selected from the group consisting of LEAFY, APETALA1 and a combination thereof, wherein said plant is characterized as having accelerated flower meristem development.

2. The plant of claim 1, wherein the heterologous nucleic acid sequence further comprises a promoter.

3. The plant of claim 2, wherein the heterologous nucleic acid sequence encodes APETALA1 protein.

4. The plant of claim 2, wherein the promoter is a constitutive promoter.

5. The plant of claim 2, wherein the promoter is an inducible promoter.

6. The plant of claim 2, wherein the nucleic acid further comprises a selectable marker.

7. The plant of claim 1, wherein the plant is a dicotyledonous plant.

8. The plant of claim 1, wherein the plant is a monocotyledonous plant.

9. A plant cell derived from the plant of claim 1.

10. Plant tissue derived from the plant of claim 1.

11. A seed which germinates into a plant having in its genome a heterologous nucleic acid sequence wherein said sequence encodes a flower meristem identity protein selected from the group consisting of LEAFY, APETALA1 and a combination thereof, and wherein said seed is capable of germinating into a plant having accelerated flower meristem development.

12. A vector comprising a nucleic acid sequence comprising at least one structural gene encoding a flower meristem identity protein selected from the group consisting of LEAFY APETALA1, and a combination thereof, that accelerates flower meristem development, operably associated with a promoter.

13. The vector of claim 12, wherein the vector comprises a T-DNA derived vector.

14. The vector of claim 12, wherein the structural gene encodes LEAFY protein.

15. The vector of claim 14, further comprising a structural gene which encodes APETALA 1 protein.

16. The vector of claim 12, wherein the structural gene encodes APETALA 1 protein.

17. The vector of claim 12, wherein the promoter is a constitutive promoter.

18. The vector of claim 12, wherein the promoter is an inducible promoter.

19. The vector of claim 18, wherein the promoter is induced by chemical means.

20. A method of producing a genetically modified plant characterized as having early flower meristem development, said method comprising:

contacting a plant cell with a vector comprising a nucleic acid sequence comprising a structural gene encoding a flower meristem identify protein selected from the group consisting of LEAFY, APETALA1 and a combination thereof for modulated flower meristem development, said gene operably associated with a promoter, to obtain a transformed plant cell;

producing a plant from said transformed plant cells; and selecting a plant exhibiting said early flower meristem development.

21. The method of claim 20, wherein the contacting is by physical means.

22. The method of claim 20, wherein the contacting is by chemical means.

23. The method of claim 20, wherein the plant cell is selected from the group consisting of protoplasts, gamete producing cells, and cells which regenerate into a whole plant.

24. The method of claim 20, wherein the promoter is a constitutive promoter.

25. The method of claim 20, wherein the promoter is an inducible promoter.

26. A plant produced by the method of claim 20.

27. Plant tissue derived from a plant produced by the method of claim 20.

28. A method for modulating flower meristem development in a plant cell comprising:

contacting said plant cell with the vector of claim 12 to obtain a transformed plant cell;

growing the transformed plant cell under plant forming conditions; and inducing early floral meristem development in the plant under conditions and for a time sufficient to induce the promoter of aid vector, thereby accelerating early floral meristem development.

* * * * *